United States Patent [19]

Mayfield

[11] Patent Number: 5,076,300
[45] Date of Patent: Dec. 31, 1991

[54] DENTAL FLOSS

[76] Inventor: Walter G. Mayfield, 3809 Villa Nova, Houston, Tex. 77077

[21] Appl. No.: 554,241

[22] Filed: Jul. 17, 1990

[51] Int. Cl.⁵ .............................................. A61C 15/00
[52] U.S. Cl. .................................................... 132/321
[58] Field of Search ................................ 132/321, 329

[56] References Cited

U.S. PATENT DOCUMENTS

| | | | |
|---|---|---|---|
| 2,996,872 | 8/1961 | Porczynski | 57/140 |
| 3,247,857 | 4/1966 | Kanbar | 132/329 |
| 3,789,858 | 2/1974 | Pesce | 132/321 |
| 4,034,770 | 7/1977 | Trecker | 132/321 |
| 4,265,258 | 5/1981 | Eaton | 132/89 |
| 4,836,226 | 6/1989 | Wolak | 132/321 |

Primary Examiner—John J. Wilson
Assistant Examiner—Cindy A. Cherichetti

[57] ABSTRACT

A dental floss in which an inelastic strand is tightly wrapped around an elastic strand of a certain length and firmly tied at each end of the elastic strand is provided. To remove matter from interproximal area between tightly spaced adjacent teeth, only the inelastic strand is used, while both the inelastic and elastic strands may be used to clean the interproximal are between widely space apart adjacent teeth.

9 Claims, 2 Drawing Sheets

DENTAL FLOSS

BACKGROUND OF THE INVENTION

1. Field of the Invention

The invention relates to a dental floss for use in cleaning unwanted matter present between adjacent teeth.

2. Description of the Related Art

Dental floss is a well known article used to promote dental hygiene by removing foreign matter from the interproximal area. Commercially available dental flosses are in the form of a thin strand made from strong inelastic materials. Such dental flosses are available in both waxed and unwaxed forms.

Typically, in use, a segment of the dental floss (strand) is stretched by both hands and passed between the crowns of adjacent teeth and stroked laterally by providing back and forth motion to remove the foreign matter from the interproximal surfaces (medial and distal surfaces) of adjacent teeth and the interproximal space. Such cleaning action requires a person to apply tensile force on the dental floss by applying significant pressure on the fingers, which can be quite discomforting. Additionally, the interproximal space can vary greatly and since each commercial dental floss is of nearly constant diameter, the same dental floss becomes difficult to use throughout the mouth. It is, therefore, desirable to have a single dental floss which can be used with ease between interproximal spaces of varying width without putting significant pressure on the hands.

Several other dental flosses have been proposed to provide better cleaning with greater comfort. As an example, U.S. Pat. No. 3,789,858 discloses a dental floss in which two relatively inelastic strands are spun together. A thin strong strand is spun together with a relatively weak strand having spaced apart tufts to provide a relatively inelastic absorbent dental floss. Such a dental floss has a constant diameter and requires significant pressure to be put on the fingers during use.

Another type of dental floss is disclosed in U.S. Pat. No. 4,265,258, which contains a single strand made from multitudinous overlaid fibers of a yarn. Some of the fibers are joined to each other while the others are merely caught among other fiber. The finished product is a single strand soft dental floss which still requires great pressure on the hands during cleaning action.

The present invention addresses some of the problems associated with the commonly used dental flosses and provides a two-stranded dental floss which is easy to use and which can be adapted for use in interproximal spaces of different widths.

SUMMARY OF THE INVENTION

The invention provides for a dental floss in which a commonly used strong inelastic dental floss is tightly wrapped around a length of a highly elastic strand. The inelastic strand is firmly attached at each end of the elastic strand. When the dental floss is pulled, the elastic strand easily stretches, straightening out and applying tension to the inelastic strand which can be placed in the interproximal space for cleaning matter between relatively tightly spaced adjacent teeth. Both the inelastic and elastic strands may be placed in the interproximal space when the adjacent teeth are widely spaced apart.

Examples of the more important features of the invention thus have been summarized rather broadly in order that the detailed description thereof that follows may be better understood, and in order that the contribution to the art may be better appreciated. There are, of course, additional features of the invention that will be described hereinafter and which will form the subject of the claims appended hereto.

DESCRIPTION OF THE DRAWINGS

For detailed understanding of the present invention, reference should be made to the following detailed description of the preferred embodiment, taken together with the accompanying drawing, in which like elements have been given like numerals and wherein.

DESCRIPTION OF THE PREFERRED EMBODIMENT

Figure 1:
FIG. 1 Shows a commonly used single strand dental floss.

FIG. 1 Shows a length of a commonly used, commercially available, polyfilamentary dental floss 10, which is relatively inelastic (distensible) and may be waxed or unwaxed. The diameter of the dental floss 10 is such that it can be made to pass between the crowns of tightly spaced adjacent teeth when a certain pressure is applied on it. The diameter of the dental floss 10 is substantially unaffected when a tensile (pulling) force is applied to the ends of a segment during use. The dental floss 10 maybe made from any of the relatively strong inflexible strand materials that are used in conventional dental flosses, such as, polyester, nylon or polyamide filaments.

Figure 2:
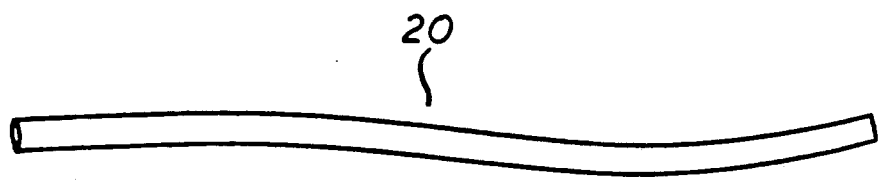
FIG. 2 Shows a strand of an elastic material.

FIG. 2 Shows a segment of an elastic strand 20. Strand 20 may be made from any highly elastic material, including materials commonly used for rubber bands. The crosssectional width of the strand 20 can vary, but is preferably a few order magnitude greater than the diameter of the strand 10 of FIG. 1. The strand 20 may be round, square, rectangular or of any suitable shape.

Figure 3:
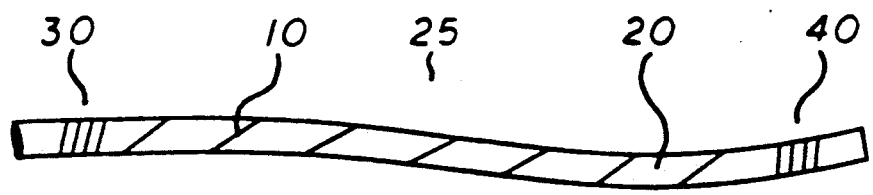
FIG. 3 Shows the strands of FIG. 1 and FIG. 2 intertwined forming the finished product of the present invention.

The strand 10 is tightly wrapped in a "candy cane or helical fashion" around the rubber strand 20 and then firmly connected at both ends 30 and 40 of the rubber strand 20 as shown in FIG. 3. The strand 10 may be rigidly affixed to the ends of the rubber strand 20 by any appropriate means, such as wrapping the strand 10 at each end of the rubber strand 20 and then fusing them together or by gluing, etc., etc. It has been found that rigidly affixing the inelastic strand 10 to the elastic strand 20 at spaced apart points makes the dental floss 25 easier to use; however, the dental floss 25 may be made in a continuous form without affixing the inelastic strand 10 to the elastic strand 20 or in a circular form by joining together the two ends of the inelastic strand.

Figure 4:
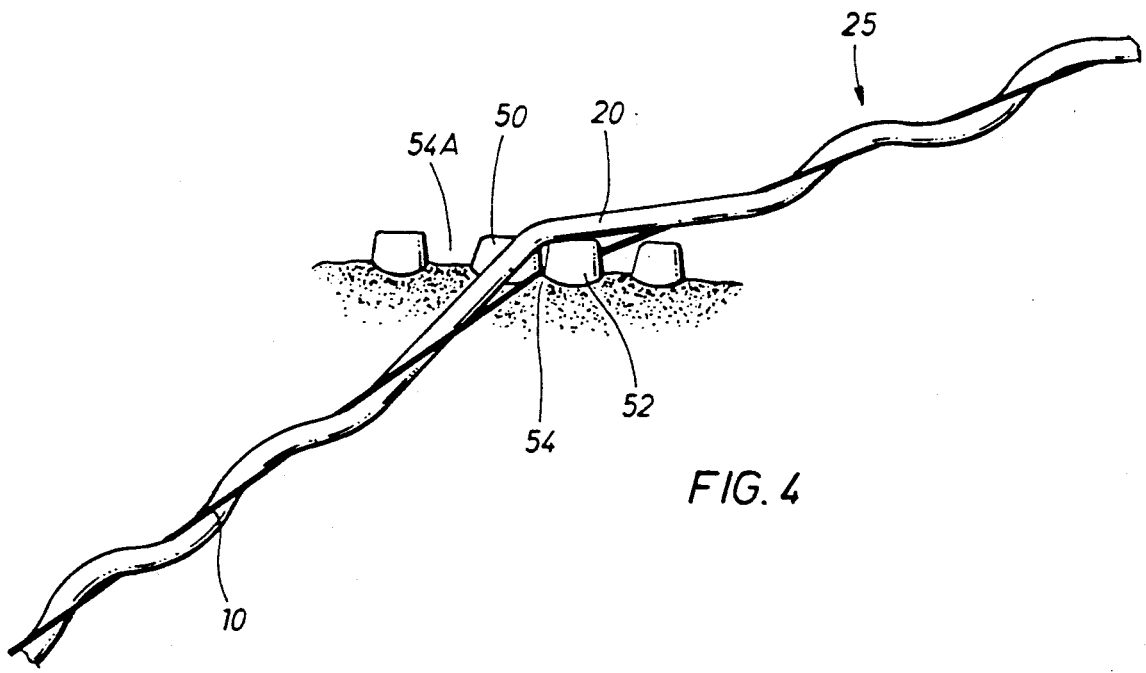
FIG. 4 Shows the use of the dental floss of FIG. 3 when adjacent teeth are tightly spaced.

FIG. 4 Shows floss of this invention when it is used to clean matter between tightly spaced adjacent teeth 50 and 52. The dental floss is pulled at ends 30 and 40 or at any two convenient points therebetween, thereby stretching the rubber strand 20 and straightening out and applying tension to the inelastic strand 10. The strand 10 is made to fall in the interproximal space 54.

A back and forth action is applied on the dental floss 25 which imparts similar motion to the strand 10 for cleaning the matter from the interproximal surfaces and the interproximal space.

Figure 5:
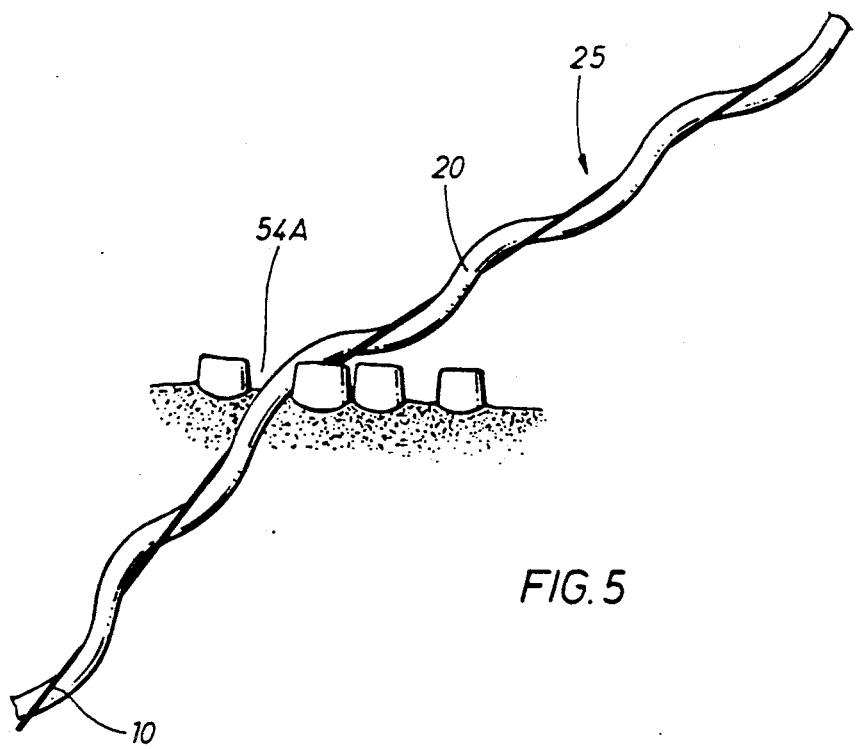
FIG. 5 Shows the use of the dental floss of FIG. 3 when adjacent teeth are widely spaced.

On the other hand, when the interproximal space is large, as shown in FIG. 5, both strands 20 and 10 fall in the interproximal space 54a. A back and forth action is applied to the dental floss 25 to provide cleaning. The strand 10, which remains relatively tightly wrapped around the rubber strand 20 and the abrasive nature of the rubber strand 20 itself provide the necessary cleaning. Thus, the dental floss 25 of the present invention functions similar to a thin commonly used dental floss when adjacent teeth are relatively tightly spaced but without exerting great pulling force on the hands, and as a thick dental floss when the adjacent teeth are farther apart, still without exerting great force on the hand as is required by when conventional dental flosses are used.

While the invention has been described with reference to the preferred embodiment, it will be obvious to one skilled in the art that numerous modifications and changes can be made without departing from the scope and spirit of the invention. It is intended that the following claims embrace all such modifications and changes.

What is claimed is:

1. A dental floss comprising a relatively inelastic strand helically wrapped around an elastic strand for providing cleaning action between adjacent teeth.

2. A dental floss comprising a relatively inelastic strand helically wrapped around an elastic strand, said inelastic strand attached to spaced apart points on the elastic strand.

3. A dental floss comprising:
   (a) An elastic strand of substantially uniform thickness having a first and second end; and
   (b) A substantially inelastic strand helically wrapped around said elastic strand and connected to the first and second ends to form said dental floss so that when the first and second strands are pulled between first and second ends, the elastic strand stretches thereby straightening out and applying tension to the inelastic strand.

4. The dental floss as claimed in claim 3 wherein said elastic strand is made from a rubber material.

5. The dental floss as claimed in claim 3 wherein said inelastic strand is made of nylon and the elastic strand in made from a rubber material.

6. The dental floss of claim 3 wherein said connections to the first and second ends are made by tying together the inelastic and elastic strands.

7. The dental floss of claim 3 wherein the thickness of the elastic strand is greater than the inelastic strand.

8. The dental floss of claim 3 wherein the elastic strand has a rectangular crosssection.

9. The dental floss of claim 3 wherein said connections to the first and second ends are made by gluing together the inelastic and elastic strands.

* * * * *